(12) United States Patent
Bake et al.

(10) Patent No.: US 10,470,885 B2
(45) Date of Patent: Nov. 12, 2019

(54) IMPLANT FOR CARTILAGE REPAIR

(75) Inventors: Nina Bake, Lidingö (SE); Leif Ryd, Stockholm (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 0 days.

(21) Appl. No.: 13/699,090

(22) PCT Filed: May 24, 2011

(86) PCT No.: PCT/EP2011/058484
§ 371 (c)(1),
(2), (4) Date: Jan. 17, 2013

(87) PCT Pub. No.: WO2011/147836
PCT Pub. Date: Dec. 1, 2011

(65) Prior Publication Data
US 2013/0110252 A1 May 2, 2013

Related U.S. Application Data

(60) Provisional application No. 61/347,650, filed on May 24, 2010.

(30) Foreign Application Priority Data

May 24, 2010 (EP) .................................. 10163721.3

(51) Int. Cl.
*A61F 2/30* (2006.01)
*A61F 2/28* (2006.01)
*B33Y 80/00* (2015.01)

(52) U.S. Cl.
CPC ................ *A61F 2/28* (2013.01); *B33Y 80/00* (2014.12)

(58) Field of Classification Search
CPC .. A61F 2310/00598; A61F 2310/00796; A61F 2/30756; A61F 2002/30757–30766; A61F 2310/00964; A61F 2002/30751
(Continued)

(56) References Cited

U.S. PATENT DOCUMENTS 5,370,700 A 12/1994 Sarkisian et al.
5,427,631 A 6/1995 Johansson et al.
(Continued)

FOREIGN PATENT DOCUMENTS

EP 1 277 450 1/2003
EP 1 698 307 A1 9/2006
(Continued)

OTHER PUBLICATIONS

U.S. Appl. No. 13/699,150, Bake et al.
(Continued)

*Primary Examiner* — Christopher D. Prone
(74) *Attorney, Agent, or Firm* — Drinker Biddle & Reath LLP (57) ABSTRACT

A medical implant for cartilage repair at an articulating surface of a joint includes a contoured, substantially plate shaped, implant body and at least one extending post. The implant body has an articulate surface configured to face the articulating part of the joint and a bone contact surface configured to face the bone structure of a joint, where the articulate and bone contact surfaces face mutually opposite directions and the bone contact surface is provided with the extending post. A cartilage contact surface connects the articulate and the bone contact surfaces and is configured to contact the cartilage surrounding the implant body in a joint. The cartilage contact surface has a coating that substantially only includes a bioactive material.

13 Claims, 6 Drawing Sheets

(58) Field of Classification Search
USPC ....... 606/95; 623/14.12, 16.11, 17.19, 20.14, 623/23.57, 18.11
See application file for complete search history.

(56) References Cited

U.S. PATENT DOCUMENTS

| | | | |
|---|---|---|---|
| 5,702,448 | A | 12/1997 | Buechel et al. |
| 5,766,221 | A | 6/1998 | Benderev et al. |
| 5,938,686 | A | 8/1999 | Benderev et al. |
| 6,001,104 | A | 12/1999 | Benderev et al. |
| 6,261,322 | B1 * | 7/2001 | Despres, III ........ A61F 2/30767 427/2.26 |
| 6,306,142 | B1 | 10/2001 | Johanson et al. |
| 6,626,667 | B2 | 9/2003 | Sussman |
| 6,858,042 | B2 | 2/2005 | Nadler et al. |
| 7,160,331 | B2 | 1/2007 | Cooney, III et al. |
| 7,258,701 | B2 | 8/2007 | Aram et al. |
| 7,608,110 | B2 | 10/2009 | O'Driscoll et al. |
| 8,241,338 | B2 | 8/2012 | Castaneda et al. |
| 8,644,973 | B2 | 2/2014 | Bake et al. |
| 8,655,468 | B2 | 2/2014 | Bake et al. |
| 8,657,822 | B2 | 2/2014 | Bake et al. |
| 2002/0055783 | A1 * | 5/2002 | Tallarida et al. .......... 623/20.14 |
| 2002/0082704 | A1 | 6/2002 | Cerundolo |
| 2003/0065400 | A1 * | 4/2003 | Beam et al. ................ 623/23.51 |
| 2003/0100947 | A1 | 5/2003 | Nadler et al. |
| 2003/0216669 | A1 | 11/2003 | Lang et al. |
| 2004/0002766 | A1 * | 1/2004 | Hunter ................ A61F 2/30767 623/20.21 |
| 2004/0039447 | A1 | 2/2004 | Simon et al. |
| 2005/0049710 | A1 | 3/2005 | O'Driscoll et al. |
| 2005/0137600 | A1 | 6/2005 | Jacobs et al. |
| 2006/0190078 | A1 | 8/2006 | Fell |
| 2006/0198877 | A1 | 9/2006 | Steinwachs et al. |
| 2007/0021838 | A1 | 1/2007 | Dugas et al. |
| 2008/0195216 | A1 | 8/2008 | Philipp |
| 2008/0257363 | A1 | 10/2008 | Schoenefeld et al. |
| 2008/0312659 | A1 | 12/2008 | Metzger et al. |
| 2009/0209962 | A1 | 8/2009 | Jamali |
| 2009/0226068 | A1 | 9/2009 | Fitz et al. |
| 2009/0228104 | A1 * | 9/2009 | Strzepa ............... A61F 2/30756 623/14.12 |
| 2009/0254093 | A1 | 10/2009 | White et al. |
| 2009/0254367 | A1 | 10/2009 | Belcher et al. |
| 2010/0268337 | A1 | 10/2010 | Gordon et al. |
| 2011/0125277 | A1 * | 5/2011 | Nygren et al. ............. 623/20.14 |
| 2013/0073050 | A1 | 3/2013 | McEntire et al. |
| 2017/0100253 | A1 | 4/2017 | Bake et al. |

FOREIGN PATENT DOCUMENTS

| | | |
|---|---|---|
| EP | 1 704 826 | 9/2006 |
| EP | 2 116 210 | 11/2009 |
| EP | 2 389 901 A1 | 11/2011 |
| JP | H8-173523 | 7/1996 |
| JP | 2883214 | 4/1999 |
| JP | 2003-531657 | 10/2003 |
| JP | 2006-510403 | 3/2006 |
| JP | 2008-188400 | 8/2008 |
| JP | 2008-540057 | 11/2008 |
| JP | 2011-517579 | 6/2011 |
| WO | WO-97/16137 A1 | 5/1997 |
| WO | WO-0143667 A1 | 6/2001 |
| WO | WO-01/82677 A2 | 11/2001 |
| WO | 2004/049981 | 6/2004 |
| WO | 2004/075777 | 9/2004 |
| WO | WO-2006/060416 | 6/2006 |
| WO | WO-2006/060416 A2 | 6/2006 |
| WO | WO-2006/091686 A2 | 8/2006 |
| WO | WO 2006/127486 | 11/2006 |
| WO | 2007/014164 | 2/2007 |
| WO | WO-2007/092841 A2 | 8/2007 |
| WO | WO-2008/098061 A2 | 8/2008 |
| WO | WO-2008/101090 A2 | 8/2008 |
| WO | 2009/108591 | 9/2009 |
| WO | WO-2009/106816 | 9/2009 |
| WO | WO-2009/111624 | 9/2009 |
| WO | WO-2009/111626 A2 | 9/2009 |
| WO | 2009/135889 | 11/2009 |
| WO | WO 2009135889 A1 * | 11/2009 ............... A61F 2/30 |
| WO | WO-2010/114578 A1 | 10/2010 |
| WO | WO-2013/155500 A1 | 10/2013 |

OTHER PUBLICATIONS

U.S. Appl. No. 13/699,084, Bake et al.
U.S. Appl. No. 13/699,126, Bake et al.
English translation of a Summary of a Notice of Reasons for Rejection issued in corresponding Japanese patent application No. 2013-511656 dated Apr. 30, 2013 (1 page).
English translation of a Japanese Office Action dated Jun. 4, 2013 issued in corresponding Japanese patent application No. 2013-511657 (2 pages).
Notice of Reasons for Rejection dated Apr. 30, 2013 issued in corresponding Japanese patent application No. 2013-511655 (with English summary thereof) (3 pages).
Office Action issued in Swedish patent application No. 1850520-6 dated Oct. 4, 2018.
International search report and written opinion dated Jul. 17, 2019 issued in international patent application No. PCT/EP2019/060721.
Gotman et al., "Titanium nitride-based coatings on implantable medical devices", Gutmanas / Advanced Biomaterials and Devices in Medicine, Jan. 1, 2014 (Jan. 1, 2014), pp. 53-73.

* cited by examiner

IMPLANT FOR CARTILAGE REPAIR

CROSS REFERENCE TO RELATED APPLICATIONS

This application is a § 371 National Stage Application of PCT International Application No. PCT/EP2011/058484, filed May 24, 2011, and claims priority under 35 U.S.C. § 119 and/or § 365 to U.S. Provisional Application No. 61/347,650 filed May 24, 2010 and European Patent Application No. 10163721.3 filed May 24, 2010, each of which are herein incorporated by reference in their entirety.

FIELD OF THE INVENTION

This invention relates in general to the field of orthopedic implants. More particularly the present invention relates to a medical implant for cartilage repair at an articulating surface in a joint such as a knee, hip, toe and shoulder.

BACKGROUND

General Background

Traumatic and overuse disorders of the joints of the body is a common problem. The weight-bearing and articulating surfaces of for example knees and other joints, are covered with a layer of soft tissue that typically comprises a significant amount of hyaline cartilage. The cartilage is prone to damage due to disease, injury or chronic wear and causes much suffering in terms of pain or disability to move freely. It is therefore important to have efficient means and methods for repairing damaged cartilage in joints in for example knees. Large knee prostheses on the market are successful in relieving pain but there is a limit in the lifetime of the prostheses of 10-15 years.

These large prostheses have lead to the further development of smaller implants that can be implanted with less invasive surgery. In this development there has also been an effort to achieve small joint implants, suitable for repair of a small cartilage injury that have a minimal influence on the surrounding parts of the joint. In the current development such small implants are designed as thin plates, or a head, with a hard surface for facing the articulate side of the joint and a bone contacting surface for facing the bone below the damaged part of cartilage. Generally, the shape and the curvature of the articulate surface of the implant are designed to be similar to the shape and the curvature of the part of the joint where the implant is inserted. Such implants are often designed with a contoured surface head and may also have one or several extending posts in the shape of a peg or a rod projecting from the bone contacting side underneath the surface head for fastening the implant to the bone in a first fixation in connection with the implant surgery.

Specific Background

In the surgical operation of implanting such small implants it is critical that the implant is positioned in a precise manner, this first fixation is called the primary fixation and it provides a mechanical attachment of the implant directly after implantation. Primary mechanical fixation can be further reinforced with a secondary fixation of the implant to the bone tissue as the implant integrates with the underlying bone. A firm secondary fixation is promoted by coating the implant with an osteoinductive, bioactive material, for example hydroxyapatite, also called hydroxylapatite or HA, on the parts of the implant contacting the bone. The bone then grows into and/or onto the implant and is in this way fixated additionally to the bone.

Although this kind of small implant has widened the repertoire for the orthopedic surgeons when it comes to repairing smaller cartilage damages in the joints, there are unwanted scenarios in the surgery of these small implants. When an implant is inserted to replace damaged cartilage in a joint, a small space may arise between a peripheral edge of the implant and the adjoining cartilage. It has been observed that joint fluid may enter the small space between the implant and the cartilage, and flow into gaps between the bone and the implant. This may lead to a stopped or delayed integration between the bone and the implant. It may even lead to the undermining of the implant and to the detachment of the implant. Another problem that may arise is that the cartilage in the immediate vicinity of the implant may slide in relation to the implant, such that it is twisted, slides over the edge onto the top of the implant or is pressed down such that the edge and surface of the implant projects above the surface of the cartilage. This in turn may lead to irregular cartilage formation and wear damages to both the cartilage in the vicinity of the implant and to the cartilage on the opposing joint surface.

Prior Art

Examples of prior art which discloses implants where bioactive material is used on the bone contacting side of the implant to promote bone to grow onto the implant is found in the following patent publications.

EP2116210 A1 from Diamorph describes an implant component and a method for producing an implant using functionally graded sintered material composed of at least 4 layers. A top layer comprises 100 wt % biocompatible wear resistant material whereas the bone contacting side of the implant comprises bioactive material, preferably hydroxyapatite (see FIG. 2 and the abstract). The functionally graded material between the top layer and the bone contacting side comprises gradually increasing amounts of bioactive material towards the bone contacting surface.

WO2009135889 A1 from Diamorph describes an implant device for an articulating surface in a joint such as a knee, elbow or shoulder. In this piece of prior art there is shown an implant that has a primary fixation means in the shape of an extending post that comprises bioactive ceramic material. Other surfaces comprising bioactive material are facing the bone underlying the cartilage (page 4 line 10-11).

WO2007/014164 A2 describes a method for implanting a prosthetic articular surface in a joint (e.g. a knee). Hydroxyapatite material (HA) is described as an alternative of a biocompatible and osteoinductive [046] material on the surface of the bone contacting portion of the implant [042], [045].

US2004/0002766 A1 relates to metallic orthopedic implants having surfaces of a thin, dense, highly wear-resistant coating of diffusion-hardened oxidation or nitridation layer in addition to surfaces coated with one or more bioceramic or bone growth promoting materials such as one or more apatite compounds. The apatite coating is applied on bone contacting areas. The publication shows that the bioceramics may be applied to different sites on the implant, and it is preferred that the bioceramics are applied to areas of maximum contact with bone, as it is intended to promote maximum bone in-growth and on-growth [0090].

EP 1277450 A2 shows a prosthetic implant for the repair and regeneration of tissue.

OBJECT OF THE INVENTION

General Object

The general object of the invention is to solve the problem of providing an implant for cartilage repair at an articulate surface of a joint that enables the implant to integrate well with healthy cartilage as well as with underlying bone. A more specific object and a partial problem to be solved is to provide an implant that reduces or blocks joint fluid from entering into the interface between the implant and the underlying bone.

SUMMARY OF THE INVENTION

The invention is based on the findings that some bioactive substances, e.g. hydroxyapatite (HA), bone morphogenetic protein (BMP), beta tricalcium phosphate (TCP) or alfa tricalcium phosphate (TCP) has the ability to stimulate cartilage growth and regeneration, in addition to the previously well known ability to stimulate growth in bone tissue. In order to solve the above stated problems the inventors have designed an implant with a cartilage contacting rim coated with a bioactive material, e.g. HA, TCP and/or BMP, and thereby achieved an implant with a potential for better fixation in the joint and a longer life time.

In a first aspect, the inventive concept comprises a medical implant (1) for cartilage repair at an articulating surface of a joint, comprising a contoured, substantially plate shaped implant body (11) and at least one extending post (8). The implant body has an articulate surface (3) configured to face the articulating part of the joint and a bone contact surface (6) configured to face the bone structure of a joint, where the bone contact surface (6) is provided with the extending post (8) and said articulate (3) and bone contact (6) surfaces face mutually opposite directions. A cartilage contact surface (7) connects the articulate (3) and the bone contact (6) surfaces and is configured to contact the cartilage surrounding the implant body (11) in a joint. The cartilage contact surface (7) has a coating substantially consisting of a bioactive material.

In an embodiment of the invention the bioactive material is any of hydroxyapatite (HA), titanium (Ti), titanium alloys, bone morphogenetic protein (BMP), beta tricalcium phosphate (TCP), collagens, fibronectin, osteonectin, calcium sulphate, calcium phosphate, calcium aluminates, calcium silicates, calcium carbonates or bioactive glass, or combinations thereof. In an aspect of the invention the bioactive material is capable of stimulating cartilage growth and regeneration. Preferably the bioactive material is any of hydroxyapatite (HA), titanium (Ti), bone morphogenetic protein (BMP) and/or beta tricalcium phosphate (TCP), most preferably the bioactive material is hydroxyapatite (HA).

Further varieties of the inventive concept comprise such an implant comprising any of the following optional individual or combinable aspects:

The bone contact surface (6) is coated or partly coated with bioactive material.

The extending post is coated or partly coated with bioactive material.

The bioactive material of the bone contact surface (6) and or extending post (8) is any of hydroxyapatite (HA), titanium (Ti), bone morphogenetic protein (BMP), beta tricalcium phosphate (TCP), collagens, fibronectin, osteonectin, calcium sulphate, calcium phosphate, calcium aluminates, calcium silicates, calcium carbonates, bioactive glass or bisphosphonates, or combinations thereof.

The extending post is not coated with bioactive material.

The articulate surface (3) substantially corresponds to the curvature of the articulating surface at the site of the diseased cartilage.

The coating of the cartilage contact surface (7) and/or bone contact surface (6) and/or extending post (8) consists of more than 95% hydroxyapatite according to XRD.

The bone contact surface or the cartilage contact surface or both has a double coating, comprising an inner coating of titanium and a surface coating of hydroxyapatite and/or tricalcium phosphate.

BRIEF DESCRIPTION OF THE FIGURES

The present invention will be further explained below with reference to the accompanying drawings, in which.

DETAILED DESCRIPTION OF THE INVENTION

Introduction

The present invention relates to a new medical implant for replacing or repairing damaged, diseased or injured cartilage in an articulating surface of a joint. The implant has a cartilage contact surface, intended to contact the cartilage in a joint, which is coated with a bioactive material capable of stimulating cartilage growth and regeneration. The implant alleviates problems discussed in the background, by promoting cartilage on-growth to the implant. By this feature the implant becomes more integrated with the cartilage surface, yielding a more stabilized interaction and firmer attachment between the implant and the cartilage. Thereby cartilage damage in the vicinity of the implant is decreased. Also the entering of joint fluid between the implant, cartilage and bone is reduced or prevented. In addition, a smoother transition between the cartilage and the implant may be obtained, leading to lesser wear on the opposing surface of the joint as the cartilage and the implant works as an integrated mechanical entity.

The Implant Structure

Implant Structure in General

Figure 1A:
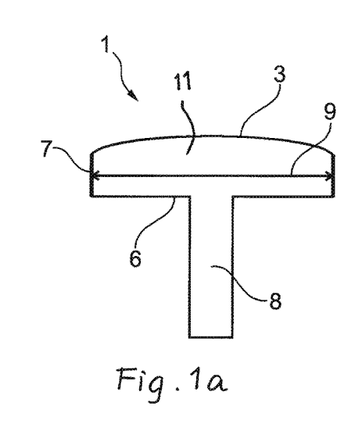
FIG. 1a shows a sectional view of an exemplifying embodiment of the implant of the present invention with the cartilage contact surface coated with hydroxyapatite.

FIG. 1a shows an exemplifying embodiment of an implant 1 according to the present invention. The implant 1 comprises a contoured, substantially plate shaped implant body 11 and an extending post 8 extending from the implant body 11. The implant body 11 has an articulate surface 3, configured to face the articulating part of the joint, and a bone contact surface 6, configured to face the bone structure of the joint. Between these surfaces of the plate shaped body 11 of the implant 1 there is a cartilage contact surface 7, on the rim or border that connects the articulate and the bone contact surfaces. The cartilage contact surface 7 is configured to face or contact the cartilage, and optionally also the bone, surrounding the implant when the implant is inserted in a joint such as a knee, toe, hip, elbow or shoulder. The cartilage contact surface is coated with a bioactive material, such as a hydroxyapatite coating.

The implant is placed in the joint after removal of the damaged cartilage and optionally, but preferably, formation of a recess in the bone under the cartilage damage, e.g. by reaming. The implant is secured in the bone first by primary attachment, by means of the extending post 8 which fits in a drill hole in the bone. The implant is also secured by a long-term secondary fixation mechanism where cartilage and/or bone tissue is grown into and/or onto the parts of the implant coated with bioactive material.

Details of the Implant Structure

Implant Body

The implant 1 comprises a contoured, substantially plate shaped implant body 11. The implant body 11 has a thin, plate-like design, meaning that its cross-sectional distance 9 is larger or even substantially larger than its thickness 4, e.g. at least 1.5 times larger. The plate can vary in size and shape and may be adjusted to the size and shape of the damaged cartilage tissue and to the needs of particular treatment situations. For instance the cross-section of the implant body 11 may have a circular or roughly circular, oval, triangular, square or irregular shape, preferably a shape without sharp edges. The size of the implant 1 may also vary. The surface area of the implant body 11 varies in different realizations of the invention between 0.5 $cm^2$ and 20 $cm^2$, between 0.5 $cm^2$ and 15 $cm^2$, between 0.5 $cm^2$ and 10 $cm^2$ or between about 1-10 $cm^2$, preferably between 0.5 $cm^2$ and 5 $cm^2$. In general, small implants are preferred since they have a smaller impact on the joint at the site of incision and are also more easily implanted which leads to smaller open surgical procedures. The primary factor for determining the size of the implant is however the nature of the lesion in the cartilage to be repaired. The thickness 4 of the implant body 11 is between 1 mm and about 10 mm, preferably between about 2 mm and 5 mm. The thickness of the implant body 11 should on the whole preferably match the thickness of the original cartilage layer, possibly also adapted to adjust for the recess in the bone, used for anchorage of the implant or formed as a part of the disease process. The articulate surface and the cartilage surrounding the implant have, because of the prepared precise fit of the implant in the implant site, corresponding heights.

Articulate Surface

The implant body 11 has an articulate surface 3 configured to face the articulating part of the joint. The articulate surface 3 comprises a biocompatible metal, metal alloy or ceramic. More specifically it can consist of any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate surface 3 comprises a cobalt chrome alloy (CoCr), pyrolytic carbon stainless steel, or a ceramic material.

It should also be understood that the articulate surface 3 may also be further surface treated in order to e.g. achieve an even more durable surface or a surface with a lower friction coefficient. Such treatments may include, for example, polishing, micro machining, heat treatment, precipitation hardening or depositing a suitable surface coating.

Bone Contact Surface

The implant body 11 has a bone contact surface 6, configured to face or contact the bone structure of the joint. In one embodiment the bone contact surface 6 comprises a biocompatible metal, metal alloy or ceramic, such as any of the metals, metal alloys or ceramic described above for the articulate surface 3. Preferably the bone contact surface 6 comprises a cobalt chrome alloy (CoCr) or stainless steel.

In one embodiment the bone contact surface 6 comprises, or in one specific embodiment is coated with, a bioactive material. In an alternative embodiment of the invention the bone contact surface does not comprise a bioactive material and/or is uncoated.

The bioactive material of the bone contact surface, if present, preferably stimulates bone to grow into and/or onto the implant surface. Several bioactive materials that have a stimulating effect on bone growth are known and have been used to promote adherence between implants and bone. Examples of such prior art bioactive materials include bioactive glass, bioactive ceramics and biomolecules such as collagens, fibronectin, osteonectin and various growth factors, e.g. bone morphogenetic protein (BMP). A commonly used bioactive material in the field of implant technology is the bioactive ceramic hydroxyapatite (HA), chemical formula $Ca_{10}(PO_4)_6(OH)_2$. HA is the major mineral constituent of bone and is able to slowly bond with bone in vivo. Thus, HA coatings have been developed for medical implants to promote bone attachment. Other bioactive ceramics include calcium sulphate, calcium phosphate, calcium aluminates, calcium silicates, calcium carbonates or combinations thereof, or bioactive glass. Bioactive glasses, generally comprising $SiO_2$, $CaSiO_3$, $P_2O_5$, $Na_2O$ and/or $CaO$ and possibly other metal oxides or fluorides, are able to stimulate bone growth faster than HA.

The bioactive materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates. Bisphosphonates are substances that inhibit the catabolic process of bone. One way to bind the bisphosphonate to the surface is by coating it with HA, which it readily binds to. The implant can also simply be immersed in a bisphosphonate solution or linked with some other biocompatible molecule e.g. carbodiimides, N-hydroxysuccinimide (NHS)-esters, fibrinogen, collagen etc.

The bone contact surface may also be further modified with fluoro compounds to enhance the bioactivity of the surface.

Figure 1B:
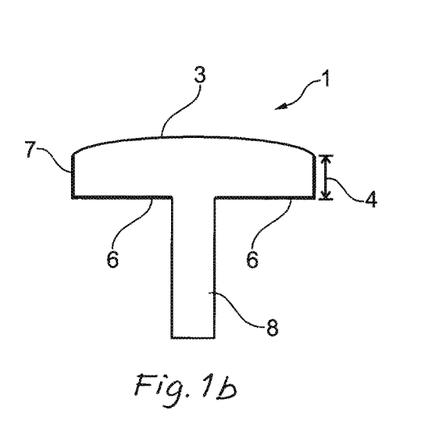
FIG. 1b shows a sectional view of an exemplifying embodiment of the implant of the present invention with both the bone contact and the cartilage contact surfaces coated with hydroxyapatite.

In one embodiment the bone contact surface 6 is coated with a double coating. Such double coating may for instance comprise an inner coating comprising titanium (Ti). The second, outer coating, that is configured to contact the bone, is preferably a HA coating containing more than 95% HA or 95-99.5% HA, or a coating comprising tricalcium phosphate (TCP) in combination with HA. By this design even more long-term fixation of the implant is achieved, since bone in- or on-growth to the implant is further stimulated by the titanium, even if the more brittle and/or soluble HA and/or TCP would eventually shed or dissolve.

Cartilage Contact Surface

Between the articulate surface 3 and the bone contact surface 6 of the plate shaped body 11 there is a cartilage contact surface 7 on the rim or border which connects the articulate and the bone contact surfaces. The cartilage contact surface 7 is configured to face or contact the cartilage surrounding the implant and optionally also the bone underlying the cartilage layer when the implant is inserted in a joint for example in the knee. The cartilage contact surface 7 is coated with a bioactive material, such as any of bioactive materials described above for the bone contact surface 6. Preferably the bioactive material is capable of stimulating cartilage growth, regeneration and attachment. The bioactive surface promotes adhesion of the implant to the surrounding cartilage surface. Such bioactive materials include hydroxyapatite (HA), titanium (Ti), bone morphogenetic protein (BMP) or beta tricalcium phosphate (TCP), separately or in combination. In a preferred embodiment the bioactive material of the cartilage contact surface 3 is hydroxyapatite (HA) and/or beta tricalcium phosphate (TCP).

In one embodiment the cartilage contact surface 7 is coated with a double coating, such as described for the bone contact surface 6 above. Such double coating may for instance comprise an inner coating comprising titanium (Ti). The second, outer coating, that is configured to contact the bone, is preferably a HA coating containing more than 95% HA or 95-99.5% HA, or a coating comprising tricalcium phosphate (TCP), or a combination of HA and TCP.

Using a bioactive material such as hydroxyapatite as a coating on the cartilage contact surface 7 of the implant has the effect that the implant, after insertion at the implant site with primary fixation, is fixated by a secondary fixation mechanism where the cartilage grows together with the bioactive coating of the implant, creating a smooth sealed surface without any holes or where joint fluid can pass. This would lead to an implant that stays in the right place and that is not prone to be undermined by joint fluids. Also, the smooth surface, where the implant and the surrounding cartilage may act as an integrated mechanical entity, reduces or prevents wear damage on the surface of the opposing side of the joint.

The height 4 of the cartilage contact surface 7 corresponds to at least 75% of the thickness of the cartilage at the site of implant insertion in the joint. More preferably the height 4 of the cartilage contact surface 7 corresponds to the height of the cartilage surrounding the implant site plus the height of an area reamed out from the underlying bone in order to fit and fix the implant. The height 4 of the cartilage contact surface 7 may vary between said extremes. Typically the height 4 of the cartilage contact surface 7 is between 0.5 and 8 mm, preferably between 1 and 5 mm.

The bioactive coating on the cartilage contact surface 7 is preferably provided all the way around the cartilage contact surface 7 on the rim of the plate shaped implant body 11. The coating is intended to be in direct contact with the surrounding cartilage and bone of a joint once the implant is implanted in the cartilage of a joint, for example a knee. The coating covers 60-100%, more preferably 80-100% and most preferably 90-100% of the cartilage contacting surface 7. In another embodiment the surface is coated such that the height 4 all around the rim of the implant body 11 is 80-100%, preferably 90-100% covered, counting from the bone contact surface 6 and upwards. In still another embodiment the coating covers most of the cartilage contact surface 7, except for an uncoated section 0.5-1 mm at the top of the height 4, adjacent to the articulate surface 3. By keeping the section closest to the articulate surface uncoated shedding of the bioactive material onto the cartilage surface surrounding the implant is prevented/reduced, thereby reducing the risk of wear from the shed material onto the joint surfaces.

The coating technique used is thermal spraying; in particular, air plasma spraying is the method which is used for producing these hydroxyapatite coatings on the implant. Another alternative is Vacuum Plasma Spray coating (VPS). In a hydroxyapatite embodiment the coating contains more than 95% hydroxyapatite by XRD after heating of alternatively the coating or the hydroxyapatite coating contains 95-99.5% hydroxyapatite.

Extending Post

Figure 1C:
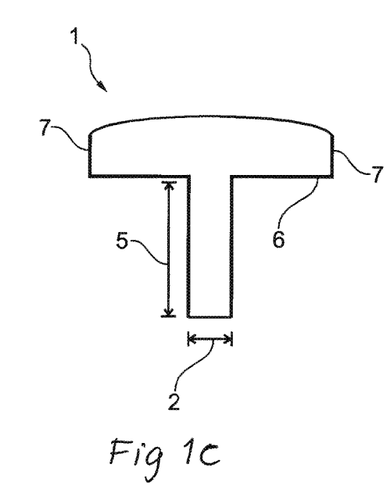
FIG. 1c shows a sectional view of an exemplifying embodiment of the implant of the present invention with the bone contact and the cartilage contact surface and also the extending post coated with hydroxyapatite.
Figure 1D:
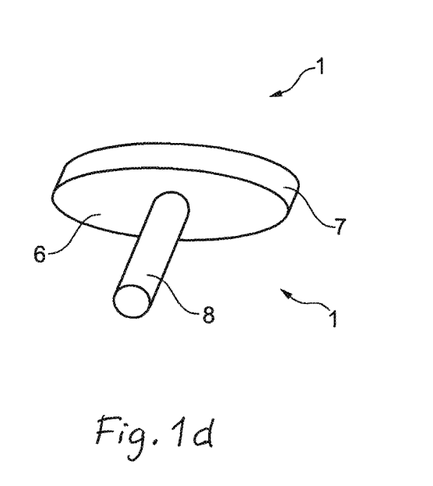
FIG. 1d shows a perspective view of an implant according to FIG. 1a and shows an embodiment of the present invention having a hydroxyapatite coating on the cartilage contact surface.

The implant body 11 may have one or several extending posts 8 which extend from the bone contact surface 6. In order to promote an immediate attachment of the implant to the bone as it is implanted into the body, the extending post 8 is used for immediate, mechanical attachment, called primary fixation. The extending post 8 has a physical structure in the form of for example a cylinder or other shapes such as one or more of a small screw, peg, keel, barb or the like. The implant body 11 and the extending post(s) 8 may be manufactured as a single, integral piece or as separate pieces that are joined by some kind of attachment means, e.g. glue or by a threaded joint.

The primary fixation means 4 may comprise e.g. the metal, metal alloy or ceramic, as in the articulate surface 3.

The extending post 8 can in one aspect of the invention be coated with a bioactive material such as described for the bone contact surface 6 above. In another aspect of the invention the extending post is uncoated.

In one embodiment the extending post 8 comprises uncoated titanium (Ti) and the cartilage contact surface 7 are coated with hydroxyapatite (HA) or a double coating with an inner coating comprising titanium (Ti) and an outer coating comprising HA, tricalcium phosphate (TCP), or a combination of HA and TCP.

An implant which does not have a coating on the extending post 8, and thus lacks a secondary fixation of the extending post, is suitable for repairing a cartilage damage in for example a hip joint where a lot of pressure is applied on the placed implant and where there is a need for an implant which reduces the risk for tensions when the mechanical pressure is high. By avoiding coating of the extending post, the extending post is thus not attached to the bone; the mechanical forces are in this way not directed into the bone part through the extending post (which may lead to tensions in the bone structure). The mechanical forces are directed to the bone through the implant head only which reduces the risk for tensions in the bone on the implant site.

Manufacturing of the Implant

An implant according to the present invention may be manufactured in predetermined, standard shapes and sizes or be tailor made for specific patients. A variety of manufacturing processes are conceivable, including, casting, molding, sintering or turning/cutting a blank e.g. with laser etc.

In one embodiment the implant according to the present invention the articulate surface 3 may be formed in a way so that it substantially corresponds to the curvature of the articulating surface at the site of the diseased cartilage and such that it is adapted to a particular individual and its cartilage damage. Techniques for obtaining such 3D images, of either the cartilage or the underlying bone or both may also include X-rays, optical coherence tomography, SPECT, PET, MR and ultrasound imaging techniques. The 3D images are used for measuring the reconstruction of the bone and the thickness and/or curvature of the cartilage and for determining the position, size and contour of damaged cartilage or cartilage loss.

A technique for making these tailor made implants is selective laser sintering (SLS). SLS is an additive manufacturing technique that uses a high power laser (for example, a carbon dioxide laser) to fuse small particles of plastic, metal (Direct metal laser sintering), ceramic, or glass powders into a mass representing a desired 3-dimensional object. The laser selectively fuses powdered material by scanning cross-sections generated from a 3-D digital description of the part (for example from a CAD file or scan data) on the surface of a powder bed. After each cross-section is scanned, the powder bed is lowered by one layer thickness, a new layer of material is applied on top, and the process is repeated until the part is completed. Or, the 3D surfaces are formed with a high precision lathe, a machine in which work is rotated about a horizontal axis and shaped by a fixed tool. The 3D surfaces can also be reamed using the digital data.

The implant is not made of porous material.

Manufacturing of an implant according to the invention may be performed using the design method according to the invention (see below) in combination with using a technique for making the implant is selected from selective laser sintering (SLS) (see above).

Design Method of the Implant

A method of designing an implant (1) for cartilage repair in an articulating surface of a joint, comprising the steps of:
I. determining physical parameters for cartilage damage in a joint and generating design parameters for an implant (1) and its placement comprising:
   a) obtaining image data representing a three dimensional image of a bone member of the joint;
   b) identifying in the obtained image data and individual cartilage damage in an articulate surface of the bone member;
   c) determining based on the obtained image data the location of the individual cartilage damage;
   d) determining based on the obtained image data the size and shape of the individual cartilage damage;
   e) determining a cartilage damage site based on the determined size and shape of the cartilage damage;
   f) determining based on the obtained image data the surface contour curvature of the individual cartilage damage site (92) and/or the subchondral bone in the joint in the predetermined area comprising the individual cartilage damage site;
   g) determining a representation of a healthy surface contour curvature comprising the individual cartilage damage site
   h) selecting an implant (1) to fit the individual cartilage damage site wherein the implant (1) has;
      a cross sectional area adapted to fit the surface area of the cartilage damage site
      an articulate surface (3) intended to align with the articular cartilage surface in the joint, based on the healthy surface contour curvature
      a cartilage contact surface (7), connecting the articulate (3) and a bone contact (6) surface, which is configured to contact the cartilage surrounding the implant body (11) the individual joint and wherein the cartilage contact surface (7) is designed to have a coating substantially consisting of a bioactive material.
II. generating design parameters of the implant (1), comprising the following steps;
   a. generating the contact points for a cartilage contact surface (7) of an implant body (11) dependent on said determined surface contour curvature of the cartilage and/or the subchondral bone in the joint in a predetermined area comprising and surrounding the site of cartilage damage, such that said cartilage contact surface (7) of the implant body (11) fits to said surface contour of the cartilage or the subchondral bone in the joint.
   b. generating the design parameters for where bioactive material is to be placed on the implant body (11) depending on the design of the cartilage contact surfaces.

In another embodiment regarding the method of designing an implant (1) for cartilage repair in an articulating surface of a joint the bioactive material is any of hydroxyapatite (HA), titanium (Ti), bone morphogenetic protein (BMP), beta tricalcium phosphate (TCP), collagens, fibronectin, osteonectin, calcium sulphate, calcium phosphate, calcium aluminates, calcium silicates, calcium carbonates, bioactive glass or bisphosphonates, or combinations thereof.

The techniques for obtaining images according to the method of the invention, of either the cartilage or the underlying bone or both may be selected from X-rays, optical coherence tomography, SPECT, PET, MR, ultrasound imaging techniques and CT (computed tomography).

PRACTICAL EXAMPLE OF THE INVENTION

Example 1

Implants 1 according to the invention were tested on adult sheep, approximately 1.5 years old;

Defects in the medial femoral condyles in the knee of the sheep were created.

Implants were inserted to replace the created defect areas in the medial femoral condyles.

Figure 2:
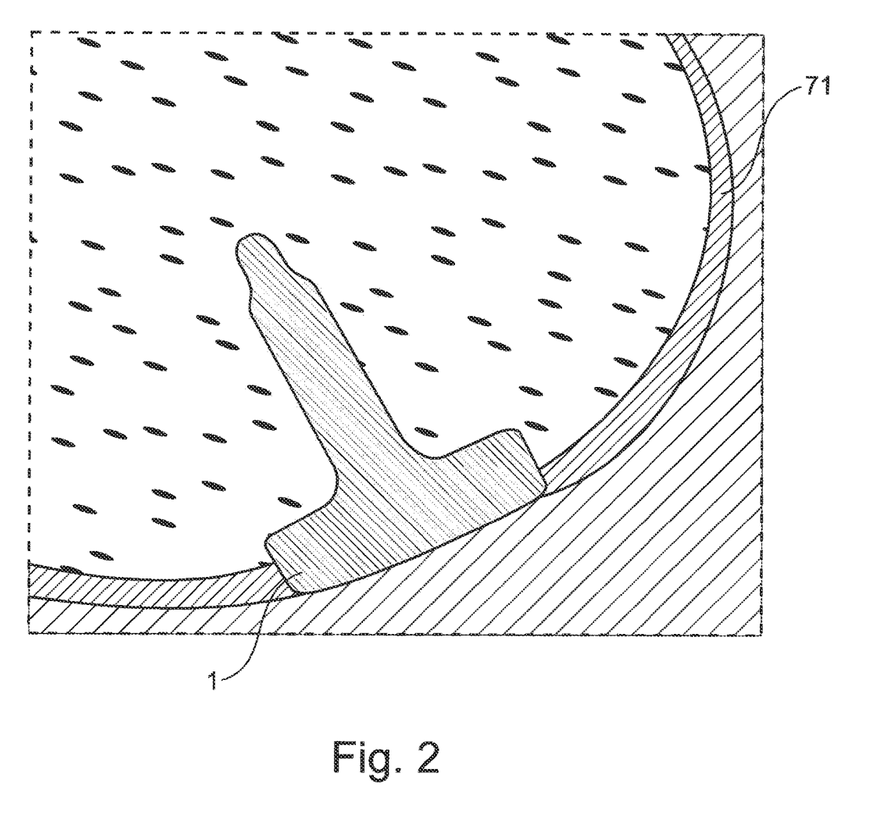
FIG. 2 shows a schematic view of the coated implant according to the invention inserted in the bone and cartilage surface of a joint.
Figure 3:
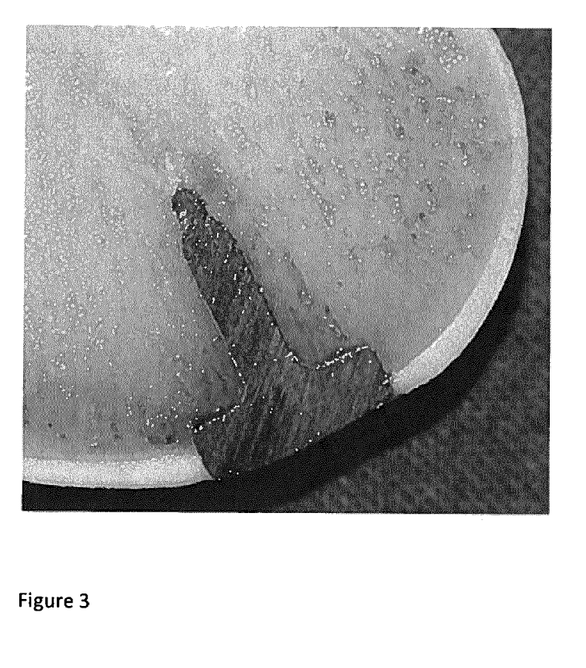
FIG. 3 shows a photo of the coated implant according to the invention inserted in the bone and cartilage surface of a joint.

Implants were retrieved and checked by taking histological preparations from the implant site after 6 weeks and after 3 months from insertion. An exact series of equipment, able to cut through metal as well as bone, was used. En bloc samples were retrieved, showing a cross-section of the implantation site (see FIGS. 2 and 3). Light microscopy revealed good integration of the implants to the bone. It was also observed that the surrounding cartilage 71 had reacted with close adherence to the HA containing surface of the implant. This suggests that HA attracts also cartilage and promotes a biological activity.

Example 2

Figure 4:
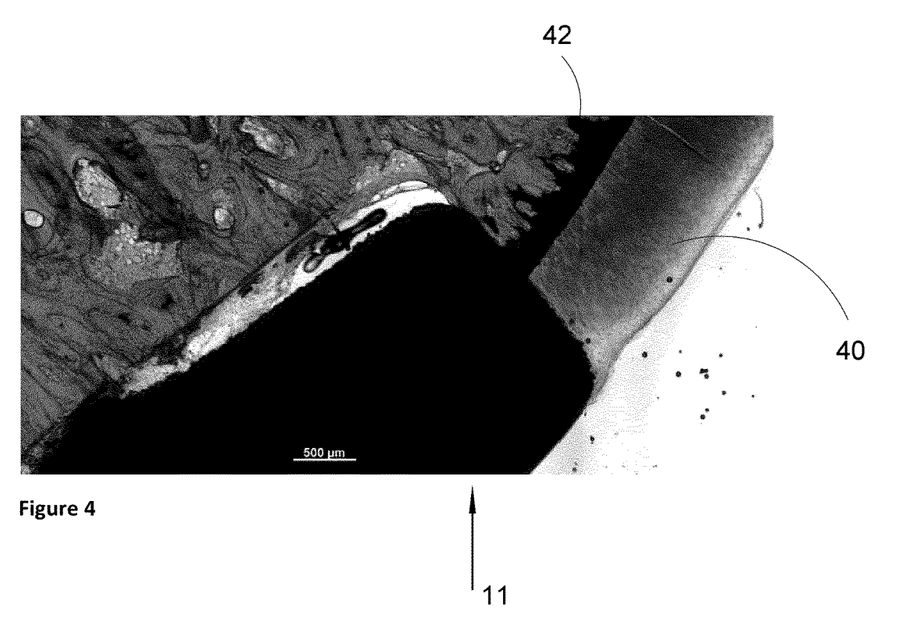
FIG. 4 shows a close up view in a photo of the coated implant according to the invention inserted in the bone and cartilage surface of a joint.

Implants 1 according to the invention were tested on adult sheep, approximately 1.5-3 years old;
Defects in the medial femoral condyles in the knee of the sheep were created.
Implants were inserted to replace the created defect areas in the medial femoral condyles.
The sheep was killed six weeks after insertion of the implant and then the implants were retrieved and checked by taking histological preparations from the implant. FIG. 4 shows a close up view in a photo of the coated implant according to the invention inserted in the bone 42 and cartilage surface of a joint in a sheep. FIG. 4 shows the implant body 11 in black and shows the close contact of the implant head with the surrounding cartilage 40. Cartilage 40 surrounding the implant body 11 is adhered to the implant body 11.

Example 3

Figure 5:
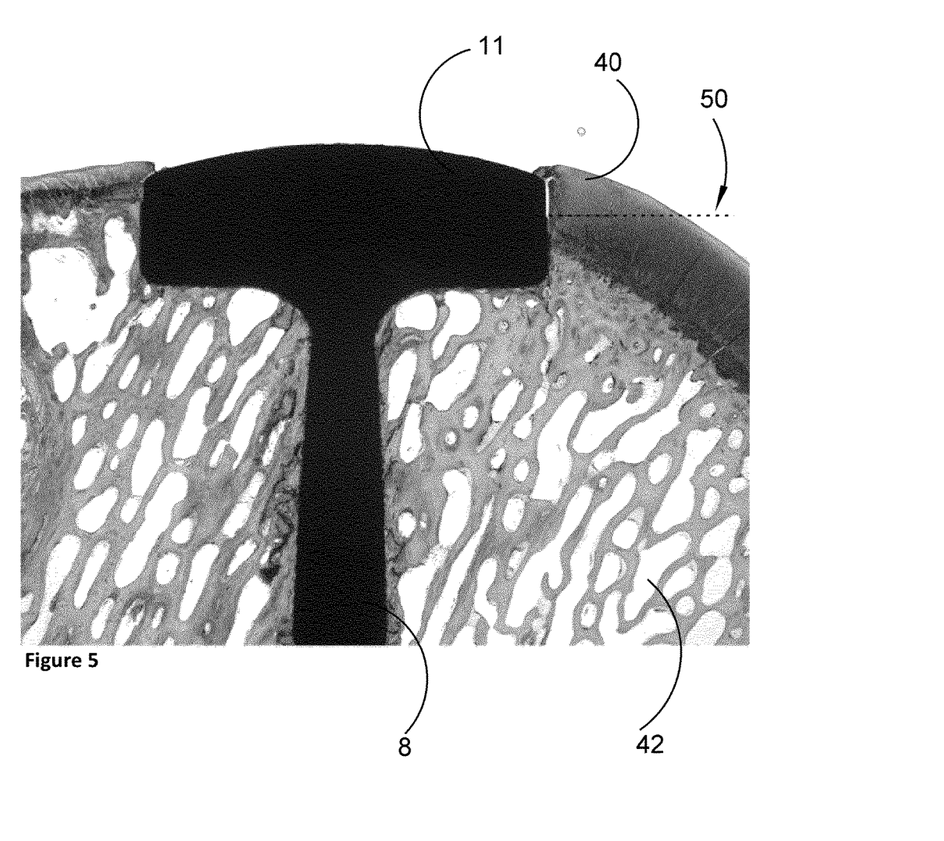
FIG. 5 shows a photo of the coated implant according to the invention inserted in the bone and cartilage surface of a joint.
Figure 6:
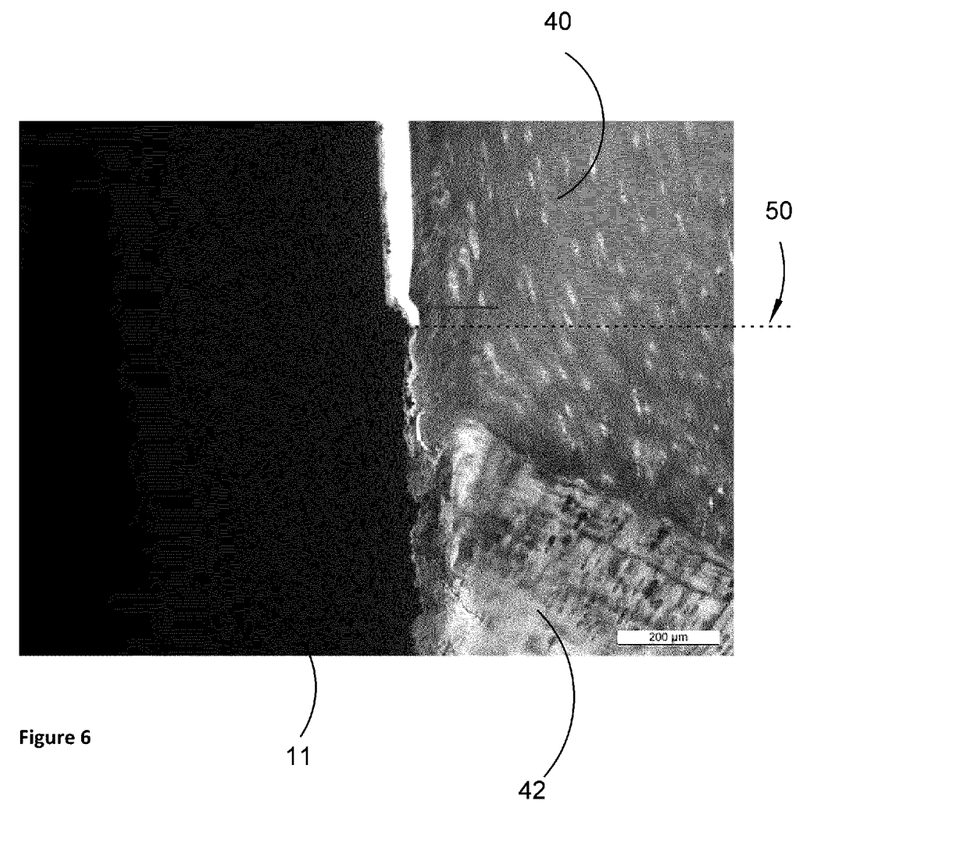
FIG. 6 shows a photo of the coated implant according to the invention inserted in the bone and cartilage surface of a joint.

Implants 1 according to the invention were tested on adult sheep, approximately 1.5-3
Defects in the medial femoral condyles in the knee of the sheep were created.
Implants were inserted to replace the created defect areas in the medial femoral condyles.
FIG. 5 shows an implant 1 in a sheep which was killed 6 months after insertion of the implant in the bone and cartilage in the joint of a sheep. The arrow 50 is pointing at the border above where HA is no longer present on the implant body 11. From FIG. 6, which is an enhancement of the implant body area in FIG. 3, it can be seen that the HA coated part (below the arrow 50 boarder) of the implant body 11 is in close contact with bone 42 and cartilage 40.

The invention claimed is:

1. A medical implant for cartilage repair at an articulating surface of a joint, comprising:
a single, integral piece comprising a contoured, substantially plate shaped, implant body portion and at least one extending post portion,
wherein said implant body portion has:
a) an articulating surface configured to face the articulating part of the joint;
b) a bone contact surface configured to face the bone structure of a joint, said articulating and bone contact surfaces facing mutually opposite directions; and
c) a cartilage contact surface, connecting the articulating and the bone contact surfaces, which is configured to contact the cartilage surrounding the implant body portion in a joint,
wherein 60-100% of the cartilage contact surface is coated with a material consisting essentially of hydroxyapatite or 60-100% of the cartilage contact surface is coated with a double coating, wherein the double coating comprises an inner coating of titanium and a surface coating consisting essentially of hydroxyapatite,
wherein the at least one extending post portion joins the implant body portion at the bone contact surface, and
wherein said implant is not made of porous material.

2. The medical implant of claim 1, wherein the coating on the cartilage contact surface is capable of stimulating cartilage growth and regeneration.

3. The medical implant according according to claim 2, wherein said coating on the cartilage contact surface is hydroxyapatite.

4. The medical implant of claim 1, wherein said coating on the cartilage contact surface consists of 95-99.5% hydroxyapatite according to X-ray diffraction.

5. The medical implant according to claim 1, wherein said bone contact surface is coated or partly coated with bioactive material.

6. The medical implant according to claim 5, wherein said bioactive material of the bone contact surface is any of hydroxyapatite, titanium, bone morphogenetic protein, beta tricalcium phosphate, collagens, fibronectin, osteonectin, calcium sulphate, calcium phosphate, calcium aluminates, calcium silicates, calcium carbonates, bioactive glass or bisphosphonates, or combinations thereof.

7. The medical implant according to claim 5, wherein the coating of the bone contact surface consists of more than 95% hydroxyapatite according to X-ray diffraction.

8. The medical implant according to claim 1, wherein said extending post portion is coated or partly coated with bioactive material.

9. The medical implant according to claim 8, wherein said bioactive material of the extending post portion is any of hydroxyapatite, titanium, bone morphogenetic protein, beta tricalcium phosphate, collagens, fibronectin, osteonectin, calcium sulphate, calcium phosphate, calcium aluminates, calcium silicates, calcium carbonates, bioactive glass or bisphosphonates, or combinations thereof.

10. The medical implant according to claim 8, wherein the coating of the extending post portion consists of more than 95% hydroxyapatite according to X-ray diffraction.

11. The medical implant according to claim 1, wherein said extending post portion is not coated with bioactive material.

12. The medical implant according to claim 1, wherein said coating on the cartilage contacting surface consists of more than 95% hydroxyapatite according to X-ray diffraction.

13. The medical implant according to claim 1, wherein the bone contact surface has a double coating, wherein the double coating comprises an inner coating of titanium and a surface coating of hydroxyapatite and/or tricalcium phosphate.

* * * * *